(12) United States Patent
Mordehai et al.

(10) Patent No.: US 8,653,446 B1
(45) Date of Patent: Feb. 18, 2014

(54) METHOD AND SYSTEM FOR INCREASING USEFUL DYNAMIC RANGE OF SPECTROMETRY DEVICE

(71) Applicant: Agilent Technologies, Inc., Loveland, CO (US)

(72) Inventors: Alexander Mordehai, Santa Clara, CA (US); Edward Darland, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 13/731,573

(22) Filed: Dec. 31, 2012

(51) Int. Cl.
*H01J 49/40* (2006.01)

(52) U.S. Cl.
CPC ..................................... *H01J 49/40* (2013.01)
USPC ............ 250/281; 250/282; 250/286; 250/287

(58) Field of Classification Search
USPC .................................. 250/281, 282, 286, 287
See application file for complete search history.

(56) References Cited

U.S. PATENT DOCUMENTS 3,376,420 A * 4/1968 Frank ....................... 250/363.01
6,900,431 B2 5/2005 Belov et al.

OTHER PUBLICATIONS

Ibrahim, et al. "Automated Gain Control Ion Funnel Trap for Orthogonal Time-of-Flight Mass Spectrometry", Anal. Chem. 2008, 80, 5367-5376.

* cited by examiner

*Primary Examiner* — Kiet T Nguyen

(57) ABSTRACT

A method is provided increasing the useful dynamic range of an ion mobility spectrometry (IMS) or an IMS-mass spectrometry (IMS-MS) device. The method includes accumulating a first sample of ions over a first time interval; providing the first sample of ions to an ion detector to provide a first frame, accumulating a second sample of ions over a second time interval, where the second time interval is different than the first time interval, and providing the second sample of ions to the ion detector to provide a second frame. First data points of the first frame are selectively combined with second data points of the second frame to provide an accumulation frame of the first and second samples of ions.

20 Claims, 3 Drawing Sheets ns accumulated over the first time interval and a second frame from ions accumulated over the second time interval. The processor is configured to combine the first data points of the first frame with the second data points of the second frame to provide an accumulation frame of the first and second sample of ions.

METHOD AND SYSTEM FOR INCREASING USEFUL DYNAMIC RANGE OF SPECTROMETRY DEVICE

BACKGROUND

Conventional ion-mobility spectrometry (IMS) instruments and IMS-mass spectrometry (IMS-MS) instruments typically include an ion trap and an ion mobility separation device. An IMS-MS instrument further includes a mass analyzer, and is capable of simultaneously producing mass spectral data and ion mobility data. For example, IMS-MS instruments combined with liquid chromatography (LC) techniques provide another dimension in separation, and may simplify analysis for very complex analytical and biological samples. However, a conventional IMS or IMS-MS instrument has a useful dynamic range which is typically limited on both the low and high ends. For example, the low end may be limited due to electronic, chemical or digitization noise, and the high end may be limited by saturation of ion conversion or electronics. So, the ion detection system will have a useful "middle portion" of its range (useful dynamic range) in which the response to increasing ion intensity (abundance) is sufficiently linear for the purposes of the measurement, or stated differently, is sufficiently proportional to the ion abundance for the purposes of the measurement. The limited useful dynamic range limits the ability to analyze different ion concentrations at the same time. It is desirable to improve the effective dynamic range of IMS or IMS-MS instrument.

Attempts have been made to improve dynamic range. For example, U.S. Pat. No. 6,900,431 to Belov et al., issued May 31, 2005, discloses a system having an encoded pulsing scheme with post process decoding of the obtained data. However, the typical dynamic range extension is still limited, increasing only by a factor of about 10 or less, in practice. In another technique, disclosed by Ibrahim et al., Automated Gain Control for Orthogonal Time-of-Flight Mass Spectrometry, ANAL. CHEM. 2008, 80, pp. 5367-5376, automated gain control is used, such that trapping time in the ion trap is adjusted based on the total ion current based on the previous measurement. However, when a small ion population needs to be detected in the presence of a much larger population, this technique is inadequate.

SUMMARY

In a representative embodiment, a method is provided for increasing dynamic range of an ion mobility spectrometry (IMS) device. The method includes accumulating a first sample of ions over a first time interval, providing the first sample of ions to an ion detector to provide a first frame, accumulating a second sample of ions over a second time interval, where the second time interval is different than the first time interval, and providing the second sample of ions to the ion detector to provide a second frame. The first data points of the first frame are combined selectively with second data points of the second frame to provide an accumulation frame of the first and second samples of ions.

In another representative embodiment, a spectrometry instrument includes an ion source; an ion trap coupled to the ion source, an ion detector, and a processor. The ion trap is configured to accumulate ions over a first time interval and a second time interval that is different from the first time interval. The ion detector is configured to receive ions from the ion trap accumulated over the first time interval and to receive ions from the ion trap accumulated over the second time interval, where the ion detector provides a first frame from ions accumulated over the first time interval and a second frame from ions accumulated over the second time interval. The processor is configured to combine the first data points of the first frame with the second data points of the second frame to provide an accumulation frame of the first and second sample of ions.

BRIEF DESCRIPTION OF THE DRAWINGS

The illustrative embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
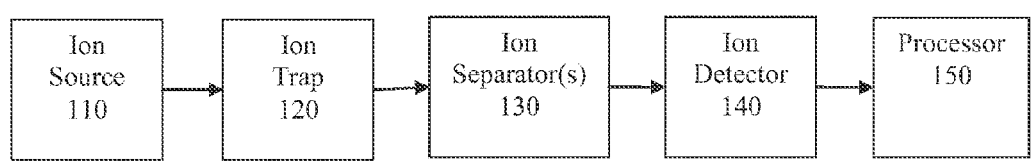
FIG. 1 is a simplified block diagram of an IMS or IMS-MS instrument, according to a representative embodiment.

In the following detailed description, for purposes of explanation and not limitation, illustrative embodiments disclosing specific details are set forth in order to provide a thorough understanding of embodiments according to the present teachings. However, it will be apparent to one having had the benefit of the present disclosure that other embodiments according to the present teachings that depart from the specific details disclosed herein remain within the scope of the appended claims. Moreover, descriptions of well-known devices and methods may be omitted so as not to obscure the description of the example embodiments. Such methods and devices are within the scope of the present teachings.

Generally, it is understood that the drawings and the various elements depicted therein are not drawn to scale. Further, relative terms, such as "above," "below," "top," "bottom," "upper," "lower," "left," "right," "vertical" and "horizontal," are used to describe the various elements' relationships to one another, as illustrated in the accompanying drawings. It is understood that these relative terms are intended to encompass different orientations of the device and/or elements in addition to the orientation depicted in the drawings. For example, if the device were inverted with respect to the view in the drawings, an element described as "above" another element, for example, would now be "below" that element. Likewise, if the device were rotated 90 degrees with respect to the view in the drawings, an element described as "vertical," for example, would now be "horizontal."

FIG. 1 is a simplified block diagram of an IMS or IMS-MS instrument, according to a representative embodiment.

Referring to FIG. 1, spectrometry instrument ("instrument") 100 may be an IMS or IMS-MS instrument, for example. The instrument 100 includes ion source 110, ion trap 120, at least one ion separator 130 and ion detector 140. In the depicted embodiment, the instrument 100 also includes processor 150, which may be implemented using a processing device, such as processor/microprocessor, a digital signal processor (DSP), one or more application specific integrated circuits (ASICs), one or more field-programmable gate arrays (FPGAs), or combinations thereof, using software, firmware, hard-wired logic circuits, or combinations thereof. In alternative configurations, the processor 150 may be separate from the instrument 100 and/or included within one or more other components of the instrument 100. The processor 150 has access to a memory (not shown), comprising a non-transitory computer readable medium for storing operating software, data and algorithms for executing the various embodiments described herein. Examples of a computer readable medium include various types of nonvolatile read only memory (ROM) and volatile random access memory (RAM), such as a disk drive, an electrically programmable read-only memory (EPROM), an electrically erasable and programmable read only memory (EEPROM), a CD, a DVD, a universal serial bus (USB) drive, and the like.

The ion source 110 may be a continuous ion source that performs electrospray ionization or another type of ionization, for example. Generally, the ion source 110 converts molecules in a sample (e.g., a mixture of chemicals) into ions. Each type of sample molecule generates one or more types of ions with characteristics that are later used by the ion separator 130 to separate the ions. Ions are generated with an abundance value that can be related to the amount of the corresponding molecule present in the original sample.

The ion trap 120 may be an accumulating/pulsing ion trap coupled to the ion source 110. For each measurement step, the ion trap 120 is configured to accumulate ions output by the ion source 110 over multiple time intervals (which may be referred to as "trapping times") corresponding to accumulation events during which ions from the ion source 110 are accumulated or trapped. Following the time interval, the trapped ions are released or pulsed from the ion trap 120 to the ion separator 130. In an embodiment, the time intervals of the accumulation events are different from one another. Also, in an embodiment, the time intervals increase for each accumulation event, such that the first time interval is the shortest and the last time interval is the longest. Alternatively, if the "stitching" of frames, discussed below, is performed after all of the data sets are acquired, the different time intervals may be performed in any order, such as the first time interval being the longest and the last time interval being the shortest, or any other order.

For each accumulation (and pulsing) event, the ion separator 130 separates the accumulated ions from one another based on characteristics of those ions. For example, in ion mobility spectrometry (IMS), the ion separation is based on the ion's collision cross-section, and the measured ion characteristics are ion drift time (related to cross-section), and ion abundance. In mass spectrometry (MS), the ion separation is based on the ion's mass-to-charge ratio (m/z), and the measured ion characteristics are the m/z and abundance. For a combined IMS-MS instrument, the ions are separated first on the basis of collision cross-section and then on the basis of m/z, so the measured characteristics are drift time, m/z and abundance. The ion detector 140 is configured to receive the separated ions from the ion separator 130 accumulated over the each of the time intervals, respectively, and to perform continuous detection on the separated ions. Based on the detection, the ion detector 140 provides frames (or data sets) respectively corresponding to the multiple time intervals. For example, the ion detector 140 may provide a first frame (first set of data) from ions accumulated over a first time interval, a second frame (second set of data) from ions accumulated over a second time interval, and a third frame (third set of data) from ions accumulated over a third time interval. The processor 150 contained within the instrument 100 is configured to receive the series of frames from the ion detector 140 corresponding to one measurement step. The processor 150 combines the series of frames into an accumulation frame to provide a composite output of the sample accumulated over an extended interval of time.

Generally, in various embodiments, the instrument 100 performs multiple measurement steps, where each measurement step includes a sequence or a series of N accumulation events performed by the ion trap 120 over corresponding intervals of time, where N is an integer greater than one. Each of the accumulation events is followed by IMS, MS or sequential IMS and MS ion separation and continuous detection of the separated ions into a corresponding frame by the ion detector 140. The individual frames of each measurement step are provided to the continuously operated processor 150, which combines the individual frames into an accumulation frame. The difference between the N accumulation events and corresponding frames within each series is the amount of time that ions are allowed to accumulate in the ion trap 120.

Figure 2:
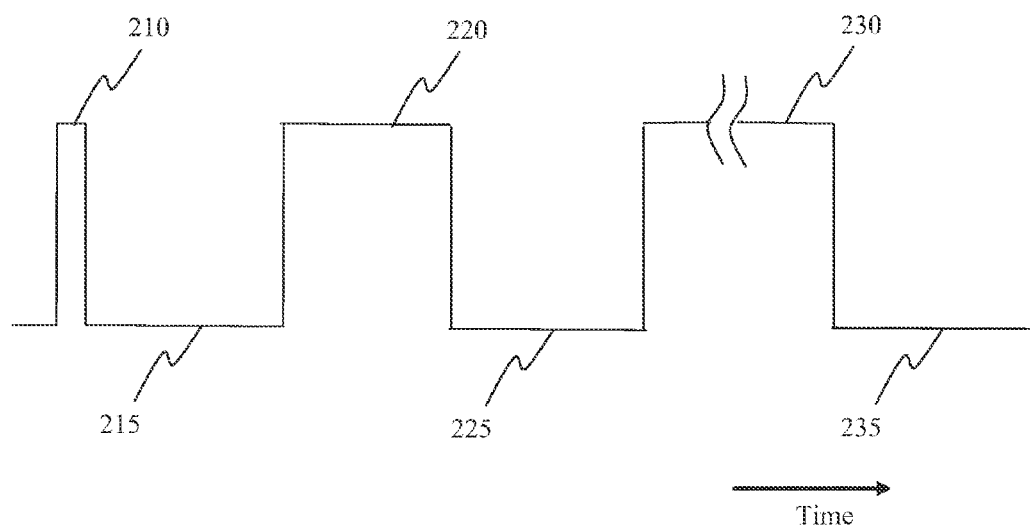
FIG. 2 is a timing diagram showing accumulation times, according to a representative embodiment.

For purposes of illustration, it may be assumed that the number of accumulation events in each measurement step is three (i.e., N=3), although it is understood that any number of accumulation events greater than one may be incorporated, without departing from the scope of the present teachings. FIG. 2 is a timing diagram showing relative accumulation time intervals of three accumulation events, according to a representative embodiment.

FIG. 2 depicts first accumulation event 210, second accumulation event 220 and third accumulation event 230, followed by corresponding first separation/detection period 215, second separation/detection period 225 and third separation/detection period 235, respectively. Each of the first through third accumulation events 210 to 230 corresponds to a trapping time (first through third time intervals) during which the ion trap 120 accumulates ions output by the ion source 110. The trapping time for the first through third accumulation events 210 to 230 are chosen to bring different portions of the ion abundance range into the useful dynamic range of the ion detector 140, ideally with some overlap.

The ratio of time intervals between adjacent accumulation events (e.g., the ratio of the longer accumulation event to the adjacent shorter accumulation event) may be selected so that ions having an abundance that is marginally above a lower end of the useful dynamic range of the ion detector 140 when acquired with the shorter accumulation time interval will be marginally below an upper end of that useful dynamic range when acquired with the longer accumulation time interval. It may be convenient computationally to arrange that the ratio of the time intervals between different accumulation events in the series to be a power of two (2, 4, 8, etc.), although other values may be incorporated without departing from the scope of the present teachings. For example, when the selected ratio is eight and the first accumulation event 210 has a corresponding trapping time of about 100 μs, then the second accumulation event 220 would have a corresponding trapping time of about 800 μs and the third accumulation event 230 would have a corresponding trapping time of about 6.4 ms. Notably, the intervening first through third separation/detection periods 215 to 235 may be approximately equal regardless of the respective lengths of the trapping times for the first through third accumulation events 210 to 230.

In comparison, a conventional IMS-MS instrument may include a series of accumulation events, but each of the accumulation events uses the same trapping time. As discussed above, such IMS-MS instruments have limited useful dynamic ranges because, for any given trapping time, only ions in some limited abundance range will fall into the useful dynamic range of the ion detector. Less abundant ions will not be detected or will be detected inaccurately (e.g., due to digitization noise), while detection of more abundant ions will be inaccurate because of detector saturation.

Figure 3:
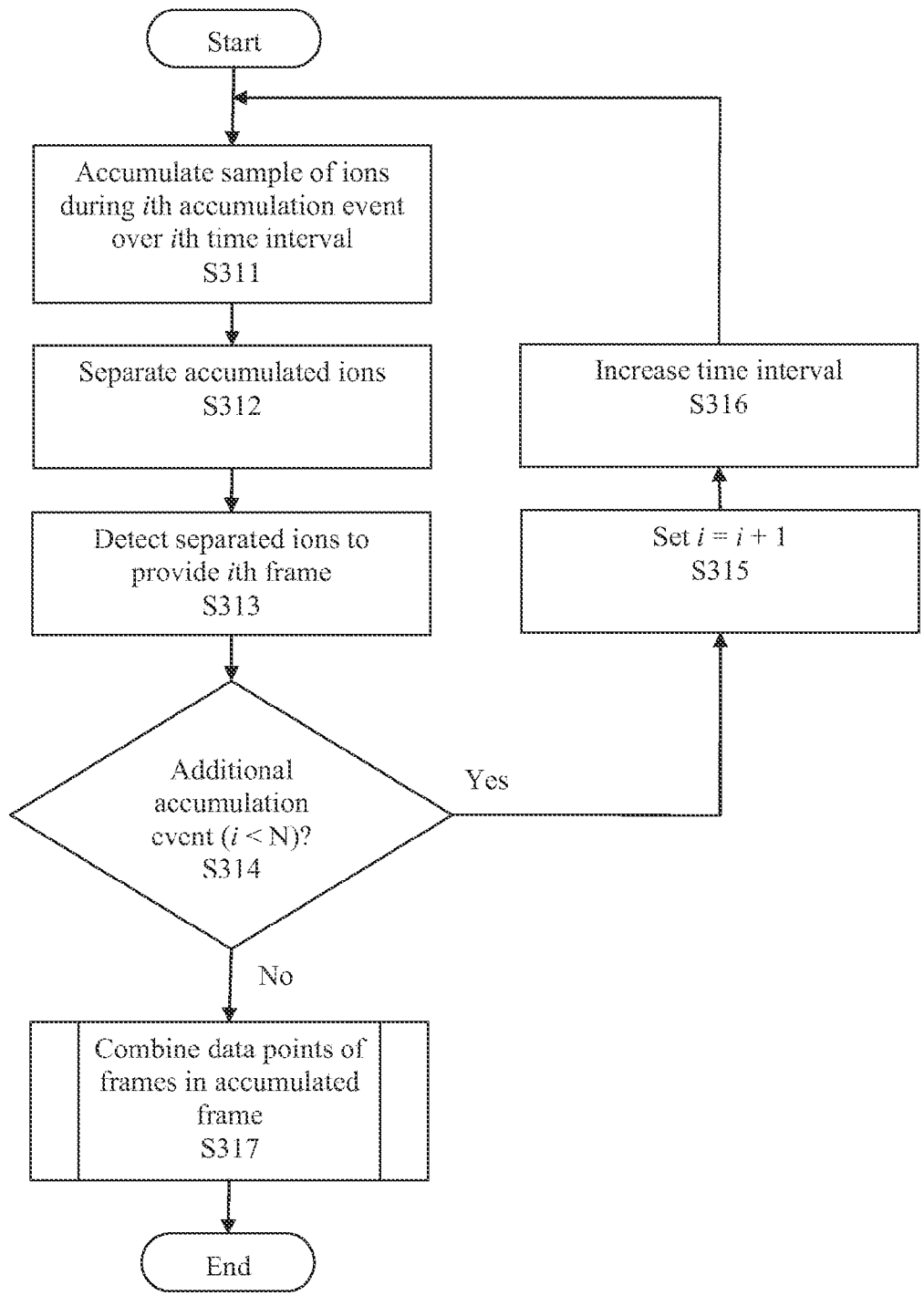
FIG. 3 is a flow diagram showing a process of providing an accumulation frame, according to a representative embodiment.

FIG. 3 is a flow diagram showing a process of providing an accumulation frame, according to a representative embodiment.

Referring to FIG. 3, in block S311, an ith sample of ions is accumulated by the ion trap 120 during an ith accumulation event, where i is a positive integer initially equal to one. The ith accumulation event has a corresponding ith time interval (or trapping time) during which the ion trap 120 accumulates ions of the ith sample. Thus, initially, a first sample of ions is accumulated over a first time interval during the first accumulation event. The first time interval is relatively short, e.g., about 100 µs, so that ions having relatively high abundance values are more likely to be captured within the useful dynamic range of the ion detector 140 (e.g., avoiding saturation). The accumulated ions are separated by the ion separator 130 in block S312, for example, based on collision cross-section, mass-to-charge ratio (m/z), or other separation characteristic. The separated ions are detected by the ion detector 140 in block S313 to provide a first frame, containing first data points indicating corresponding ion abundance values of the first sample of ions.

In block S314, it is determined whether there are additional accumulation events to be performed. For example, it may be determined whether i is less than N, where N is the number of accumulation events in each measurement step. When there are additional accumulation events (block S314: Yes), the number of the accumulation event is incremented, e.g., i is set to equal i+1 (now i=2), in block S315. The time interval for the next accumulation event is increased in block S316, such that the next time interval is longer than the previous time interval. For example, as mentioned above, the next time interval may be increased such that a ratio of the next time interval to the previous time interval may be a power of two (2, 4, 8, etc.), although other time interval increases may be incorporated without departing from the scope of the present teachings. In the present example, the longer second time interval, e.g., about 800 µs, is provided such that ions having relatively intermediate abundance values are more likely to be captured within the useful dynamic range of the ion detector 140. The process then returns to block S311, in which a second sample of ions is accumulated by the ion trap 120 during the second accumulation event over the second time interval. The accumulated ions are separated by the ion separator 130 in block S312, and the separated ions are detected by the ion detector 140 in block S313 to provide a second frame, containing second data points indicating corresponding ion abundance values of the second sample of ions.

In block S314, it is again determined whether there are additional accumulation events to be performed. When there are additional accumulation events (block S314: Yes), as in the present example, the number of the accumulation event is incremented, e.g., i is set to equal i+1 (now i=3), in block S315. The time interval for the next accumulation event is again increased in block S316, such that the next time interval is longer than the previous time interval. For example, the third time interval, e.g., about 6.4 ms, is longer than the second time interval, such that ions having relatively low abundance values are more likely to be captured within the useful dynamic range of the ion detector 140. The process then returns to block S311, in which a third sample of ions is accumulated by the ion trap 120 during the third accumulation event over the third time interval. The accumulated ions are separated by the ion separator 130 in block S312, and the separated ions are detected by the ion detector 140 in block S313 to provide a third frame, containing third data points indicating corresponding ion abundance values of the third sample of ions.

In the present example, the third accumulation event is the last accumulation event in the measurement step, although it is understood that a measurement step may include any number of accumulation events greater than one, without departing from the scope of the present teachings. When it is determined in block S314 that there are no more additional accumulation events, e.g., that i=N (block S314: No), the method proceeds to process block S317, which combines data points of each of the acquired frames into an accumulation frame formed of composite data points corresponding to the combined data points. The data points may be combined according to various normalizing techniques, one example of which is described below with reference to FIG. 4. Also, in alternative embodiments, the data points of each accumulation frame may combined into the accumulation frame following each cycle, as opposed to waiting until the data points of all of the acquired frames have been collected as shown in the illustrative embodiment of FIG. 3. The process then ends for the current measurement step, and the resulting accumulation frame contains data points over a wider virtual useful dynamic range than would otherwise be achievable using the ion detector 140 in a conventional manner.

Figure 4:
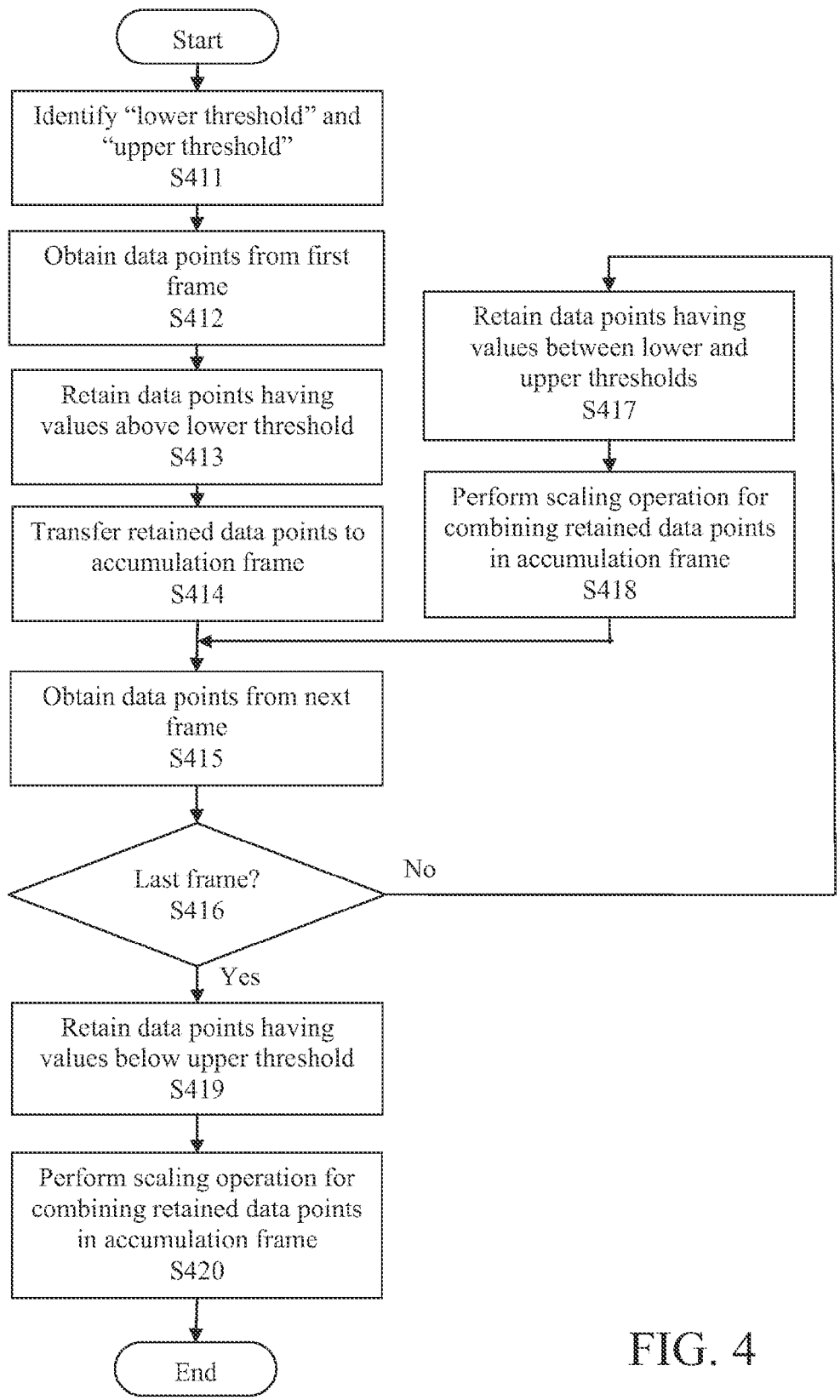
FIG. 4 is a flow diagram showing a process of combining acquired frames in an accumulation frame, according to a representative embodiment.

FIG. 4 is a flow diagram showing a process of combining acquired frames in an accumulation frame, according to a representative embodiment. More particularly, the flow diagram depicts a normalizing algorithm for knitting together the data points from the multiple frames (e.g., three frames) in order to provide the accumulation frame. Generally, each observed ion abundance in each of the acquired frames is compared with a useful abundance range for the ion detector 140 defined by two reference threshold values ("lower threshold" and "upper threshold") to determine whether and how the corresponding data points are to be included in the accumulation frame.

Referring to FIG. 4, the lower threshold and the upper threshold are identified in block S411. The lower threshold is selected to represent the value below which measured ion abundance values are not trusted because they fall below the lower limit of the useful dynamic range of the ion detector 140. For example, the lower threshold may be set to about 0.05 of the full useful dynamic range of the ion detector 140. The upper threshold is selected to represent the value above which measured ion abundance values are not trusted because they fall above the upper limit of the useful dynamic range of the ion detector 140. For example, the upper threshold may be set to about 0.90 of the full useful dynamic range. The lower and upper limits of the useful dynamic range may be dictated by the range of an analog-to-digital converter (ADC), for example, used by the ion detector 140.

In various embodiments, the accumulation frame may be stored in memory (not shown). Storage created for the accumulation frame is initially empty, and then ion abundance values are added to it from the individual frames, where the individual frames are processed in the order of shortest trapping time to longest trapping time (e.g., from the first frame to the third frame in the present example). In block S412, data points are obtained from the first frame, which is, for example, acquired during the first accumulation event discussed above. In block S413, data points in the first frame having abundance values above the lower threshold are retained, and abundance values falling below the lower threshold are removed. Notably, even data points having abundance values that exceed the upper threshold are retained for the first frame, since no other subsequent frame can have better measurements of these data points. All of the retained data points from the first frame are transferred or copied to the accumulation frame in block S414.

In block S415, data points are obtained from the next frame. It is determined in block S416 whether the next frame is the last frame. In the present example, the next frame is the second frame, obtained during the second accumulation event, as discussed above. When it is determined that the next frame is not the last frame (block S416: No), meaning that there is another frame with a longer accumulation time, the next frame is deemed to be an intermediate frame and the process proceeds to block S417. For instance, the second frame in the present example is an intermediate frame. In block S417, data points of the intermediate frame having abundance values above the lower threshold and below the upper threshold are retained. Stated differently, data points with abundance values falling below the lower threshold and above the upper threshold are removed.

A normalizing and scaling operation is performed in block S418 for combining the retained data points of the intermediate frame in the accumulation frame. In an embodiment, the operation compares the retained data points of the intermediate frame with data points already included in the accumulated frame, and determines which of the retained data points from the intermediate frame are to be included in the accumulation frame. For example, when the accumulation frame does not yet have an abundance value corresponding to a retained data point of the intermediate frame, then the retained data point is simply transferred or copied into the accumulation frame. When the accumulation frame already has an abundance value corresponding to a data point that is not retained in the intermediate frame, then the abundance value of that data point is multiplied by the ratio of the trapping time (e.g., second time interval) of the intermediate frame (e.g., the second frame) and the trapping time (e.g., first time interval) of the preceding frame (e.g., the first frame), or 800 μs/100 μs=8 in the present example, and stored in the accumulation frame. Finally, when the accumulation frame already has an abundance value corresponding to a data point that is also retained in the intermediate frame, a new abundance value of the composite data point in the accumulation frame ($AV_{new}$) may be computed according to Equation (1) below:

$$AV_{new} = \text{Ratio} * [(AV_{AF} + AV_{IF})/(\text{Ratio}+1)] \quad \text{Equation (1)}$$

In Equation (1), "Ratio" is the ratio of the trapping time (e.g., the second time interval) of the intermediate frame and the trapping time (e.g., the first time interval) of the preceding frame, or 800 μs/100 μs=8, as discussed above. "$AV_{AF}$" is the abundance value of the data point in the accumulation frame, and "$AV_{IF}$" is the abundance value of the data point in the intermediate frame. The new abundance value of the data point in the accumulation frame is thus scaled so that it fits with other values put into the accumulation frame, and weighted so that the total ion count reflects statistics.

The process then returns to block S415, where data points are obtained from the next frame. It is determined in block S416 whether the next frame is the last frame. In the present example, the next frame is the third frame, obtained during the third accumulation event, as discussed above. When it is determined that the next frame is the last frame (block S416: Yes), meaning that it has the longest accumulation time, the process proceeds to block S419. When it is again determined that the next frame is not the last frame (block S416: No), the process repeats blocks S417 and S418 for the intermediate frame, and continues this cycle in the order of next frames having increasing accumulation times until the last frame is obtained.

In the present example, the last frame is the third frame, provided during the third accumulation event. Thus, in block S419, data points in the third frame having abundance values below the upper threshold are retained, and abundance values exceeding the upper threshold are removed. Notably, even data points having abundance values that are below the lower threshold are retained, since no other previous frame can have better measurements of these data points. A scaling operation is performed in block S420 for combining the retained data points of the last frame in the accumulation frame. In an embodiment, the scaling operation compares the retained data points of the last frame with data points already included in the accumulation frame, and determines which of the retained data points from the last frame are to be included in the accumulation frame. This process may be the same as the scaling process discussed above with reference to block S418, and therefore will not be repeated. When all of the frames have been processed, the accumulation frame contains the desired "scaled and knitted" abundance values.

The data points of the acquired frame may be combined in the accumulation frame according to various processes other than the process described above with reference to FIG. 4. For example, data points of the various frames may be retained based on the lower and upper thresholds, as discussed above. However, when the accumulation frame already includes an abundance value for a particular retained data point, and/or multiple acquired frames include the same data point, a decision may be made simply to select one of the corresponding values for that data point.

Also, the retained data points of the frames may be compared to one another in order to provide the corresponding composite data point in the accumulation frame. For example, for each data point in the first frame, a one-to-one correspondence may be made with a data point in the second frame, e.g., based on a characteristic of the data points other than the ion abundance, such as ion drift time or ion drift time and m/z. The corresponding data points may be combined in a data point pair to create a normalized composite data point of the accumulation frame, where the normalized composite data point is based on the difference between the first and second time intervals.

In the embodiments discussed above, the ratio of accumulation times between adjacent frames is the same throughout the measurement process. In alternative embodiments, the ratios of accumulation times between adjacent frames may differ from one another. For example, where three frames are used to provide the accumulation frame, the respective trapping times may be 100 μs, 800 μs and 1600 μs, in which case the ratio of the trapping times between the second frame and the first frame is 8:1 and the ratio of trapping times between the third frame and the second frame is 2:1.

The various operations discussed above with reference to FIGS. 3 and 4 may be included in logic executable by a computer processor. The processing may be performed, for example, by the ion detector 140, the processor 150 and/or some combination thereof (e.g., by distributed processing). The operations may be implemented using internal logic or software, stored on a computer readable medium, and executable by one or more computer processors, ASICs, FPGAs or combinations thereof, as discussed above.

In an embodiment, the "multi-trapping" process for increasing the linear useful dynamic range described above may be combined with a multiplexing process, such as Hadamard multiplexing, or other encoding technique. Multiplexing may assist in overcoming low duty factor of an experiment in which ions may be trapped/gated for only 1 ms out of the 60 ms or more total drift time. Under appropriate conditions, the duty factor may be increased effectively by up to about 50 percent. Combining multiplexing and multi-trapping enables simultaneously increasing the signal-to-noise ratio (SNR) and the useful dynamic range.

While the disclosure references exemplary embodiments, it will be apparent to those skilled in the art that various changes and modifications may be made without departing from the spirit and scope of the present teachings. Therefore, it should be understood that the above embodiments are not limiting, but illustrative.

What is claimed is:

1. A method of increasing useful dynamic range of an ion mobility spectrometry (IMS) device, the method comprising:
   accumulating a first sample of ions over a first time interval;
   providing the first sample of ions to an ion detector to provide a first frame;
   accumulating a second sample of ions over a second time interval, wherein the second time interval is different than the first time interval;
   providing the second sample of ions to the ion detector to provide a second frame; and
   combining selectively first data points of the first frame with second data points of the second frame to provide an accumulation frame of the first and second samples of ions.

2. The method as claimed in claim 1, wherein the second time interval is greater than the first time interval, and an abundance of ions in the second sample is greater than an abundance of ions in the first sample.

3. The method as claimed in claim 1, wherein the second time interval is less than the first time interval, and an abundance of ions in the second sample is less than an abundance of ions in the first sample.

4. The method as claimed in claim 1, wherein the combining of the first data points with the second data points comprises:
   determining, for each first data point in the first frame, a one-to-one correspondence with a second data point in the second frame based on a characteristic of the first data point other than ion abundance; and
   combining the corresponding first and second data points to create a normalized composite data point in the accumulation frame, wherein the normalized composite data point is based on abundance values scaled based on the ratio of the first and second time intervals.

5. The method as claimed in claim 4, wherein the characteristic comprises an ion drift time.

6. The method as claimed in claim 4, wherein combining of the first data points of the first frame with the second data points of the second frame to provide the accumulation frame of the first and second samples of ions comprises:
   determining a useful abundance range for the ion detector, wherein the useful abundance range comprises a lower threshold, or an upper threshold, or both, and measurements below the lower threshold and above the upper threshold are not useful; and
   determining the normalized composite data point from the first and second data points in the useful abundance range.

7. The method as claimed in claim 6 wherein the determining of the normalized composite point further comprises:
   determining a weighted sum for each of the first and second data points.

8. The method as claimed in claim 6, wherein the determining of the normalized composite point further comprises:
   before the determining of the normalized composite point, discarding the first data point when its value is below the lower threshold of the useful abundance range of the ion detector;
   scaling the second data point based on the ratio of the first and second time intervals; and
   providing the scaled second data point as the normalized composite point.

9. The method as claimed in claim 6 wherein the determining of the normalized composite point further comprises:
   before the determining of the normalized composite point, discarding the second data point when its value is above the upper threshold of the useful abundance range of the ion detector;
   scaling the first data point based on the ratio of the first and second time intervals; and
   providing the scaled first data point as the normalized composite point.

10. A software program or product, embodied on a non-transitory computer readable medium, for executing the method of claim 1 when run on a processor.

11. A spectrometry instrument, comprising:
   an ion source;
   an ion trap coupled to the ion source, wherein the ion trap is configured to accumulate ions over a first time interval and a second time interval that is different from the first time interval;
   an ion detector configured to receive ions from the ion trap accumulated over the first time interval and to receive ions from the ion trap accumulated over the second time interval, wherein the ion detector provides a first frame from ions accumulated over the first time interval and a second frame from ions accumulated over the second time interval; and
   a processor configured to combine first data points of the first frame with second data points of the second frame to provide an accumulation frame of first and second samples of ions.

12. The spectrometry instrument as claimed in claim 11, wherein the second time interval is greater than the first time interval, and an abundance of ions in the second sample is greater than an abundance of ions in the first sample.

13. The spectrometry instrument as claimed in claim 11, wherein the second time interval is less than the first time interval, and an abundance of ions in the second sample is less than an abundance of ions in the first sample.

14. The spectrometry instrument as claimed in claim 11, wherein the processor is configured to determine, for each first data point in the first frame, a one-to-one correspondence with a second data point in the second frame based on a characteristic of the first data point other than an ion abundance; and to combine each pair of corresponding first and second data points from the first frame and the second frame to create a normalized composite point of the accumulation frame, wherein the normalized composite point is based on the difference between the first and second time intervals.

15. The spectrometry instrument as claimed in claim 11, wherein the processor is further configured to determine a useful abundance range for the ion detector and to determine a normalized composite output point of the accumulation frame from the first and second data points in the useful abundance range, and wherein the useful abundance range comprises a lower threshold, an upper threshold, or both, and measurements below the lower threshold and above the upper threshold are not useful.

16. The spectrometry instrument as claimed in claim 15, wherein the processor is further configured to determine, for each set of corresponding data points, a weighted sum of the data point from the first data points and the corresponding data point from the second data points.

17. The spectrometry instrument as claimed in claim 15, wherein the processor is further configured to discard a data point from the first data points when its value is below the lower threshold of the useful abundance range of the ion detector; and to provide the corresponding data point from the second data points as a normalized composite point of the accumulation frame.

18. The spectrometry instrument as claimed in claim 15, wherein the processor is further configured to discard a data point from the second data points when its value is above the upper threshold of the useful abundance range of the ion detector; and to provide the corresponding data point from the first data points as a normalized composite point of the accumulation frame.

19. The spectrometry instrument as claimed in claim 11, wherein the processor is implemented in firmware.

20. The spectrometry instrument as claimed in claim 19, wherein the firmware comprises an FPGA.

* * * * *